(12) United States Patent
Mahalingam

(10) Patent No.: US 10,463,528 B2
(45) Date of Patent: Nov. 5, 2019

(54) DISPOSABLE URINARY DEVICE

(71) Applicant: Padmanabhan Mahalingam, Chennai (IN)

(72) Inventor: Padmanabhan Mahalingam, Chennai (IN)

( * ) Notice: Subject to any disclaimer, the term of this patent is extended or adjusted under 35 U.S.C. 154(b) by 0 days.

(21) Appl. No.: 15/865,912

(22) Filed: Jan. 9, 2018

(65) Prior Publication Data
US 2019/0209360 A1    Jul. 11, 2019

(51) Int. Cl.
*A61F 5/455*    (2006.01)
*A61F 13/15*    (2006.01)

(52) U.S. Cl.
CPC ...... *A61F 5/4556* (2013.01); *A61F 13/15252* (2013.01); *A61F 2013/15146* (2013.01)

(58) Field of Classification Search
CPC .................................................. A61F 5/4556
USPC ................................ 4/144.2–144.4
See application file for complete search history.

(56) References Cited

U.S. PATENT DOCUMENTS

| | | | | |
|---|---|---|---|---|
| 2,382,276 A * | 8/1945 | Wells | ...................... | A61F 5/455 4/144.1 |
| 4,296,502 A * | 10/1981 | Bortle | .................. | A61F 5/4556 4/144.1 |
| 4,937,890 A * | 7/1990 | Tafur | .................... | A61F 5/4556 4/144.1 |
| 6,123,691 A * | 9/2000 | Karavani | .............. | A61F 5/4556 604/329 |
| 7,325,256 B1 * | 2/2008 | Pecinka, Sr. | .......... | A61F 5/4556 4/144.1 |
| 2008/0262448 A1 * | 10/2008 | Mahalingam | ......... | A61F 5/4556 604/327 |
| 2009/0056003 A1 * | 3/2009 | Ivie | ...................... | A61F 5/4556 4/144.3 |

* cited by examiner

*Primary Examiner* — Tuan N Nguyen
(74) *Attorney, Agent, or Firm* — Donald R. Boys; Central Coast Patent Agency LLC

(57) ABSTRACT

A personal urinary device for a female has a straight, round tube of biodegradable material, having one end exhibiting an angle with a plane perpendicular to an axis of the tube, a lip having a diameter larger than the outside diameter of the tube, on the outside of the tube at a first distance from an end opposite the angled end, and a rounded element at the end opposite the angled end.

18 Claims, 12 Drawing Sheets

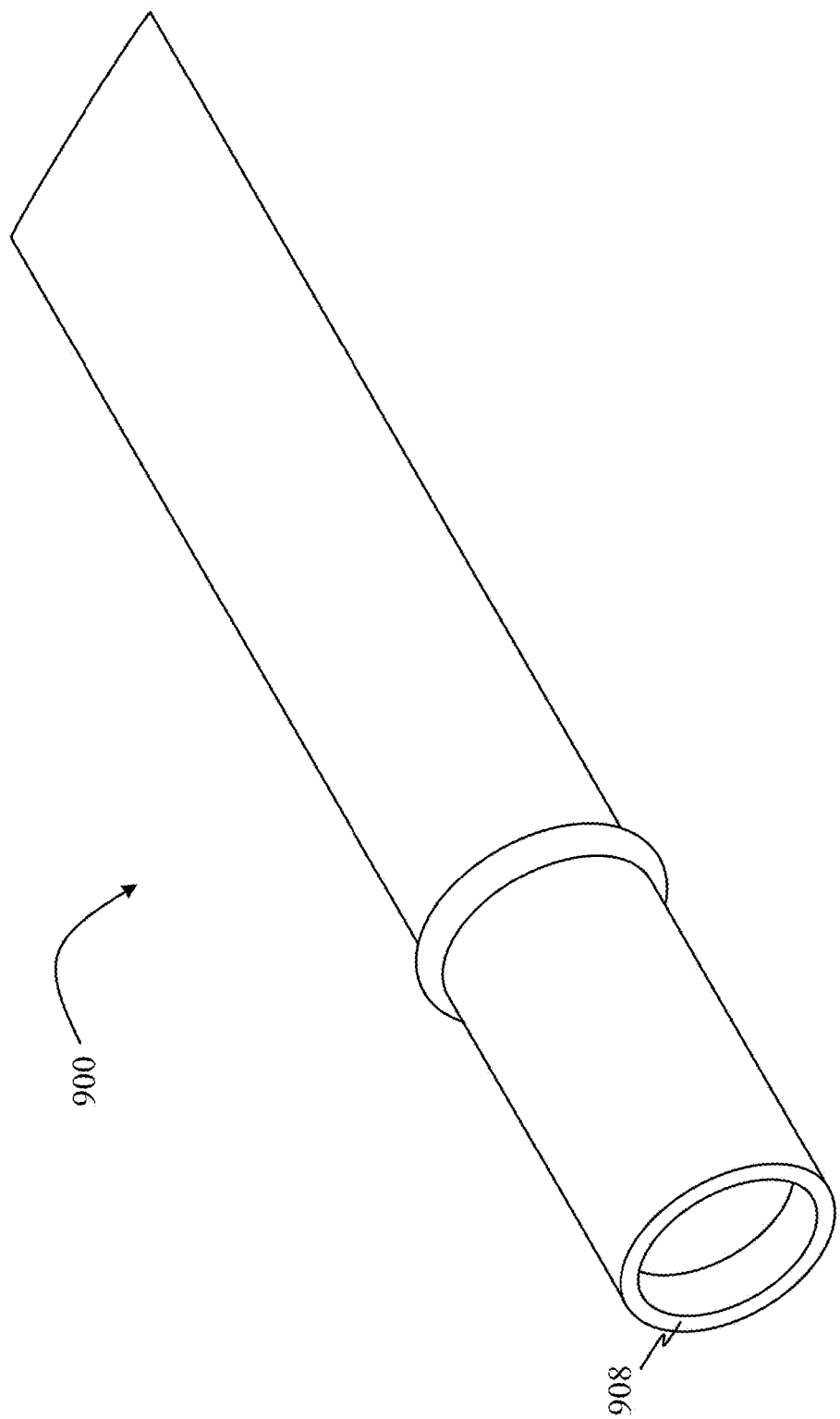

DISPOSABLE URINARY DEVICE

BACKGROUND OF THE INVENTION

1. Field of the Invention

The present invention is in the area of personal devices, and pertains more particularly to a disposable device for enabling women to urinate in a standing position with ease.

2. Description of Related Art

It is well-known that a lady cannot urinate in a standing position like a male can without soiling herself due to the nature of the female external genitalia. Women usually open their legs wide and/or bend forwards with their knees folded and urinate into a larger receptacle behind such as a water closet.

A number of devices have attempted to solve this need. They have all been based on a device whose whole contour matches the body around the external genitalia like a very large funnel. These devices were made large for easy use, but are easily soiled because of sealing devices to prevent the urine from leaking out, and cannot be personalized because of the same reasons, for example, a lady cannot carry it around like when she goes to a movie house, and if the movie house installs such a device a second person cannot use it without washing after the previous person's use. Also, due to varying body sizes, many sizes are required to suit the population.

What is clearly needed is a relatively small, hand-held urinary device that may be carried by a user, such as in a purse, so there is no need for more than one person to share the use of a single device. In some cases such a device may be adapted for either a male or a female to use. What is also clearly needed is an article of clothing adapted especially for use with such a device, such that a person, to use the urinary device, need not open the usual and conventional fly openings to place and use the urinary device. What is also clearly needed is a urinary device that may be discarded by a user after use.

BRIEF SUMMARY OF THE INVENTION

In an embodiment of the invention, a personal urinary device for a female is provided, comprising a straight, round tube of biodegradable material, having one end exhibiting an angle with a plane perpendicular to an axis of the tube, a lip having a diameter larger than the outside diameter of the tube, on the outside of the tube at a first distance from an end opposite the angled end, and a rounded element at the end opposite the angled end.

In one embodiment, the device is formed into a tube by rolling a flat sheet of paper or paperboard, curved on one end into a tube, and securing edges with an adhesive. Also in one embodiment, the lip is formed by a length of material secured across the flat sheet by an adhesive. Also in one embodiment, the tube is coated on the outside by a waterproof material. And in one embodiment, the tube is coated on both inside and outside by a waterproof material.

In one embodiment, the lip is implemented at from about three quarters of one inch to about two inches from the end opposite the angle-cut end. Also in one embodiment, the rounded element is formed by turning inward material of the tube. In one embodiment, the rounded element is formed by adding a separate piece to the end opposite the angle-cut end. And in one embodiment, the straight, round tube is formed by extrusion from plastic.

In another aspect of the invention, a method for forming personal urinary device for a female is provided, comprising forming a straight, round tube of biodegradable material, having one end exhibiting an angle with a plane perpendicular to an axis of the tube, implementing a lip having a diameter larger than the outside diameter of the tube, on the outside of the tube at a first distance from an end opposite the angled end, and forming a rounded element at the end opposite the angled end.

In one embodiment of the method, the device is formed into a tube by rolling a flat sheet, curved at one end, and securing edges with an adhesive. Also in one embodiment, the lip is formed by a length of material secured across the flat sheet by an adhesive. Also in one embodiment, the tube is coated on the outside by a waterproof material. In one embodiment, the tube is coated on both inside and outside by a waterproof material. And in one embodiment, the lip is implemented at from about three quarters of one inch to about two inches from the end opposite the angle-cut end.

In one embodiment of the method, the rounded element is formed by turning inward material of the tube. Also in one embodiment, the rounded element is formed by adding a separate piece to the end opposite the angle-cut end. And in one embodiment, the straight, round tube is formed by extrusion from plastic.

BRIEF DESCRIPTION OF THE SEVERAL VIEWS OF THE DRAWINGS

FIG. 10 is a back perspective view of the device of FIG. 9.

DETAILED DESCRIPTION OF THE INVENTION

The present invention in one embodiment comprises a relatively small, hand-held device that can go into a handbag. In this embodiment it includes a tube of predetermined size which mates directly with the female external urethral orifice. To compensate for dilation of the orifice during higher discharges, the device in this embodiment has a gutter at the mouth of the collector, which takes the effluent away from the body. Further, in this embodiment the tube has a projection that nests in the vestibule of the vulvae and helps locating. For a feeling of well being to the person, this projection also may engage with the clitoris.

Figure 1:
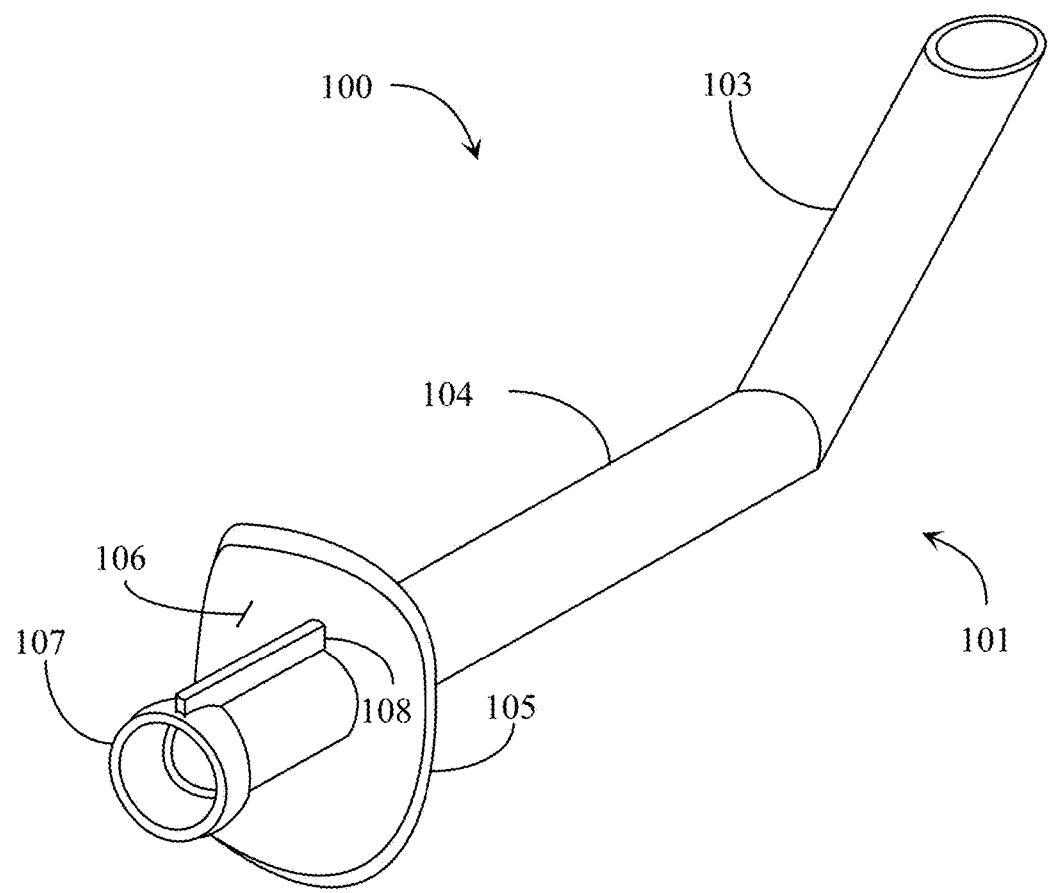
FIG. 1 is a perspective view of a female urinary device according to one embodiment of the invention.

FIG. 1 is a perspective view of a female urinary device 100 according to one embodiment of the invention. Referring now to FIG. 1, the urinary device 100 of the present invention is illustrated in perspective. Device 100 may be manufactured of one material, preferably a durable medical-grade polymer, such as by injection molding. Other rigid and semi-rigid materials may also be used like some metals and ceramics. In one embodiment, device 100 is molded in one piece from medical grade polymer. Device 100 is adapted to be used repeatedly as needed to re-direct urine out and away from the urethra, and may be cleaned and disinfected between uses.

Device 100 in a preferred embodiment includes a conduit or tubing section 101 that is formed or molded to bend at an angle creating tube section 104 and tube section 103. The bend may be relatively abrupt, as shown, or very gradual, in a sweeping curve. Tube section 104 has an annular cup 107, also referred to as a collector, formed on one open end for facilitating a snug fit over the urethra. Cup 107 may be formed on one end of conduit 101 by shaping, molding or flaring before forming the bend creating tube sections 104 and 103, depending on the method of forming or manufacture. In one embodiment, cup 107 may be a separate part that is heat welded, glued or otherwise affixed to the end of tube section 104.

In some embodiments a placement shield 105 is provided on tubing section 104 nearer to cup 107. In this example, shield 105 is positioned over the peripheral wall of tube 104 and may be glued, heat welded or otherwise formed or affixed to the peripheral wall of the tube. In some embodiments a user may manipulate placement shield 105 in order to accurately place device 100 into a suitable position for use. In some embodiments shield 105 may have a concave surface 106 on the side that faces cup 107. An important purpose of the shield is to act as a stop for a user's fingers in use. In some embodiments Shield 105 may also have a crescent-shaped profile that is curved toward cup 107 more so on the lower part of shield 105 than the upper portion of the shield. The combination of the profile of shield 105 and surface 106 provides a naturally conforming surface that conforms to the pubic mound of a user around the urethra to help prevent any leakage that may escape from cup 107.

Shield 105 is strategically positioned away from cup 107 to an amount that facilitates a comfortable fitting of cup 107 over the urethra while the shield rests either against intervening clothing or against the body. The curvature and shape of placement shield 105 may conform to the proximal curvature of the female genital area (pubic mound) or, in other embodiments, may have another shape. A support rib 108 is provided in the embodiment shown on device 100. Support rib 108 bridges the inside of placement shield 105, the top of tube section 104, and cup 107. Support rib 108 is molded, heat welded, or otherwise affixed substantially near the top center portion of the re-directing end of the device. Support rib 108 is not specifically required in order to practice the present invention, but helps a user to locate the urethra by providing an indicator of device position during the act of placing the device over the urethra.

Cup 107 is adapted to encompass or cover the urethra while the user urinates. Holding shield 105 such as with an index and middle finger of one hand holds the device in place against the urethra and the vaginal area surrounding the urethra. In use of the device, the general position and extended direction of tubing section 104 is angularly downward, for example, while a user is standing and using the device while tubing section 103 is presented at a lesser downward angle and away from the user. The exact angle of bend for sections 104 and 103 may vary, generally from zero to about forty-five degrees, however an approximate 10 to 35 degree bend angle is suitable for most users.

While a user is urinating into the device, holding the device in place with one hand, urine is redirected through tube section 104 and tube section 103 and out of the device into a urinal or other selected vessel or urinary target. A user may control the direction of a urine stream by rotating the device slightly clockwise or counter clockwise to vary the direction of tube section 103.

In one embodiment of the present invention, device 100 may be used while the user is fully clothed, as long as there is access to the urethra through one or more layers of clothing, for example, through a zipper opening, or some other opening fabricated in clothing. Also in one embodiment, device 103 may be used during menstrual periods without removing a sanitary shield as long as the shield is adapted with a flap opening of the sort that may be opened to provide access to the urethra.

Device 100 is purposely designed to be relatively small so a person may carry it discretely, for example in a purse or bag. The diameter of the cup and conduit may vary in different embodiments from about one-quarter inch to about one-half inch, and the overall length is from about four to six inches.

Figure 2:
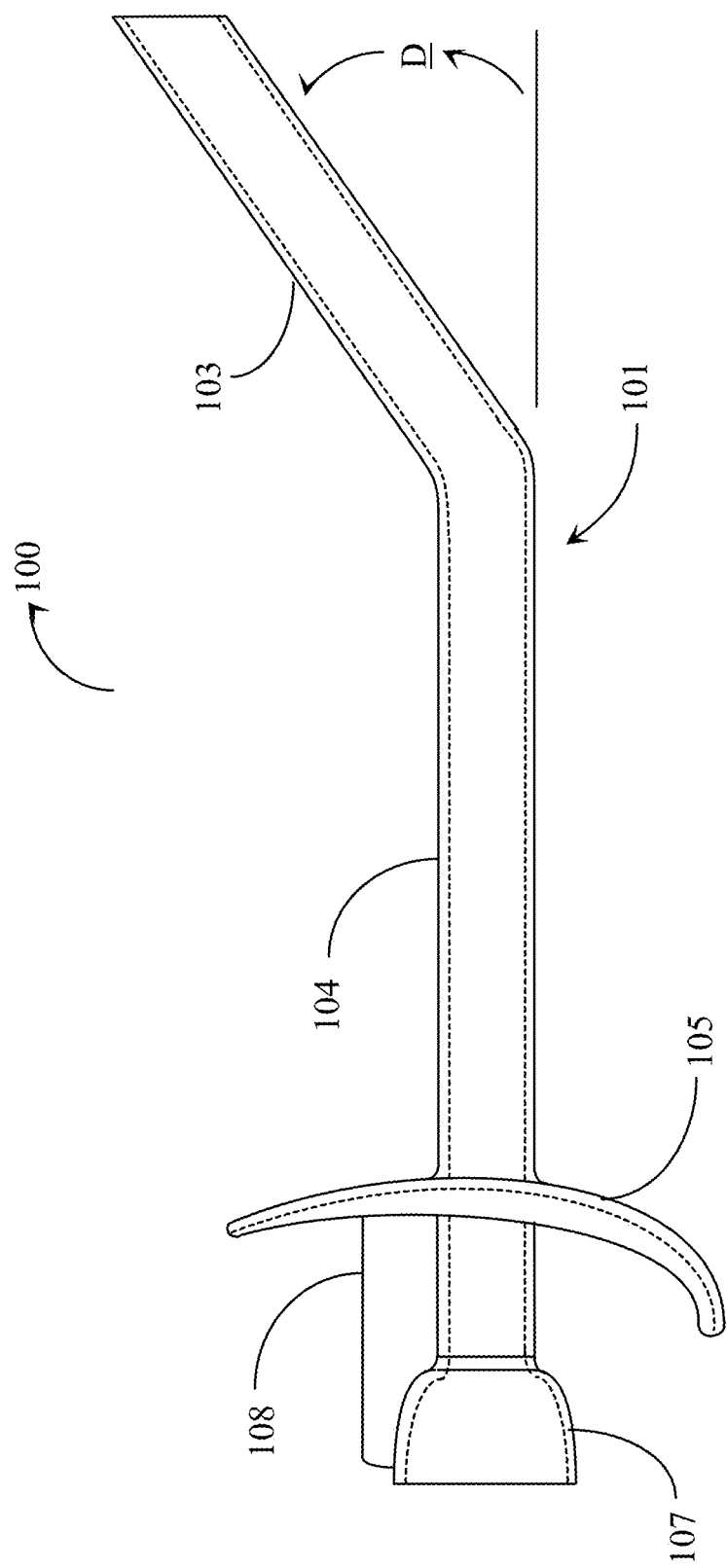
FIG. 2 is a side elevation view of the device of FIG. 1.

FIG. 2 is an elevation view of device 100 of FIG. 1. Conduit section 101 may begin as one section of plastic tubing that is flared or formed at one end to form cup 107 and may be bent to form tubing section 104 and tubing section 103 as shown. Shield 105 and support rib 108 may be provided as separate components that are attached to conduit 101 during a molding process or by some other method such as heat welding, gluing, or the like. Further, in some embodiments, cup 107 may also be a separate attachment so that one device can accommodate cups of different diameters.

The wall thickness for the conduit and for other parts of the device is largely a design choice, and a thickness of 0.1 inch has been found by the inventor to be adequate. The bend angle in device conduit 101 is illustrated herein as an angle D and may vary between zero and forty-five degrees with a nominal preference range of approximately 10 to 35 degrees. Other conduit and cup sizes as well as other angles of bend may be implemented in device 100 without departing from the spirit and scope of the present invention. Device 100 is approximately 6 inches in overall tubing length with approximately 4 inches for tubing section 104 and approximately 2 inches for tubing section 103. The exact lengths of tubing sections 104 and 103 as well as the overall length of device 100 may vary without departing from the spirit and scope of the invention.

In one embodiment of the invention, device 100 may include a gutter (not illustrated) formed on the bottom center of the device tubing, the gutter extending into the cup. The gutter may be provided as part of a molding process to help train the urine through the device faster than otherwise would be the case with a round tube.

Figure 3:
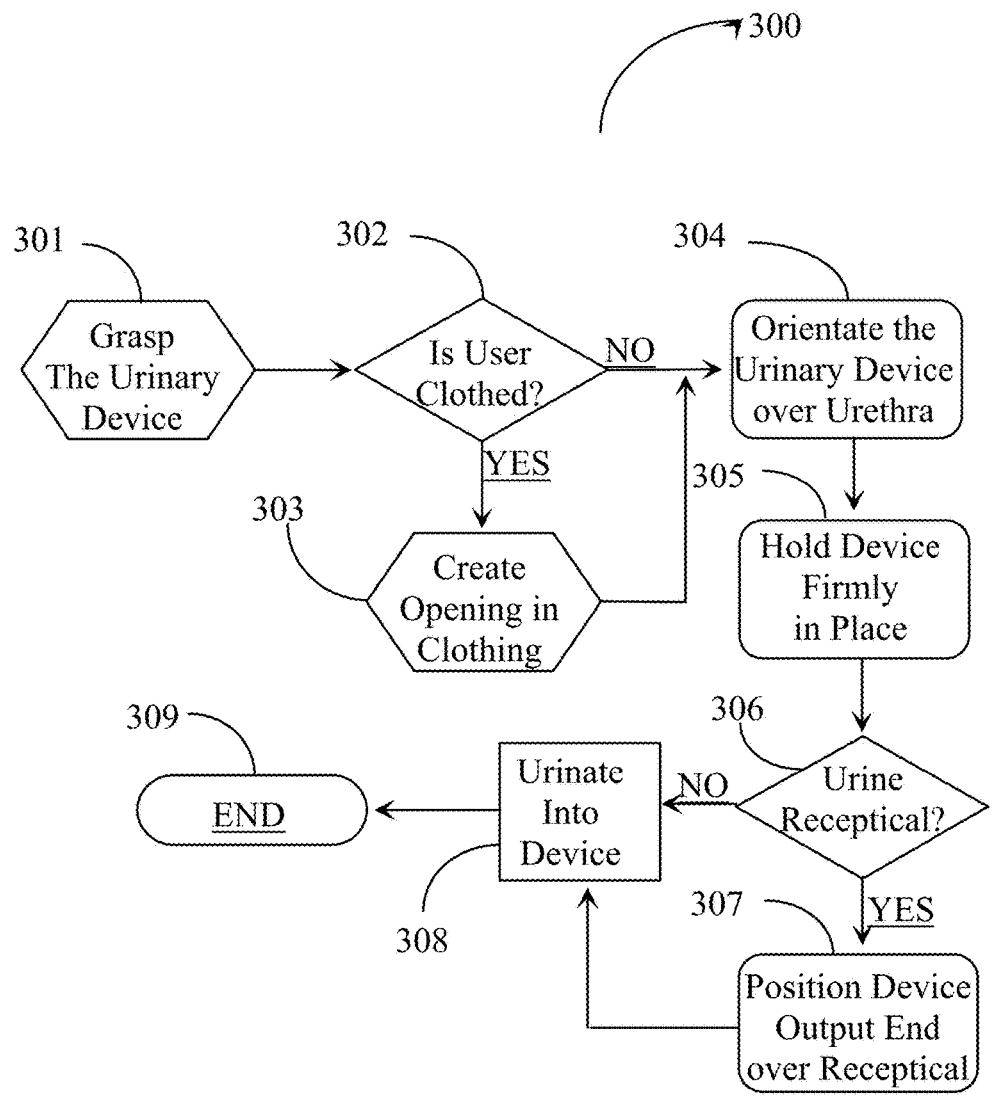
FIG. 3 is a process flow chart illustrating steps 300 for practicing the invention.

FIG. 3 is a process flow chart 300 illustrating steps for practicing the invention. At step 301 a user grasps the urinary device. At step 302 the process branches according to whether or not the user is clothed when using the device. If the user is not clothed at step 302, then the process moves to step 304 where the user orientates the device over the urethra before urinating. If the user is clothed at step 302, the process branches to step 303 where the user creates an opening in the clothing such as by unzipping trousers or the like to provide access to the urethra.

At step 304 the user orientates the device over the urethra aided by the natural curvature of the shield of the device and the position indicator rib (108) if provided. At step 305 the user holds the device firmly in place, the cup covering the urethra and the shield resting against the user.

At step 306, it is determined if the user is using a urine receptacle such as a toilet. If there is a urine receptacle that the user desires to evacuate urine into, the user positions the device output end over the receptacle at step 307 while still firmly holding the device in place over the urethra. At step 308 the user urinates into the device. If at step 306 there is no receptacle, for example, the user is outdoors in the field, the process moves directly to step 308 where the user urinates into the device. At step 308 the user remains in a standing position. At step 309 the process ends. The user may rinse the device after use and stow the device away in a case or plastic bag provided and adapted for the purpose.

In one embodiment, a version of device 100 may be provided with an enlarged conical cup in place of cup 107 so that the device may accommodate a man's genitalia. Such an enlarged cup may be shaped appropriately to accommodate the user while in either a flaccid or erect state. In one embodiment, device 100 may be provided with two separate attachment cups, one for a female such as cup 107 and a larger cup for a male. In still another embodiment, tubing 101 may be telescopic in nature so that the overall length of device 101 may be collapsed for more convenient carrying and then extended to an appropriate length for use.

In the case of a device 100 that is meant to accommodate both men and women, shield 105, used to provide and interface for a woman to manipulate the device is not required in a version of the device adapted for men using a larger cup attachment. Therefore, in one embodiment, shield 105 may be detached from the urinary device. Likewise, cup 107 may be a separate attachment.

Figure 4:
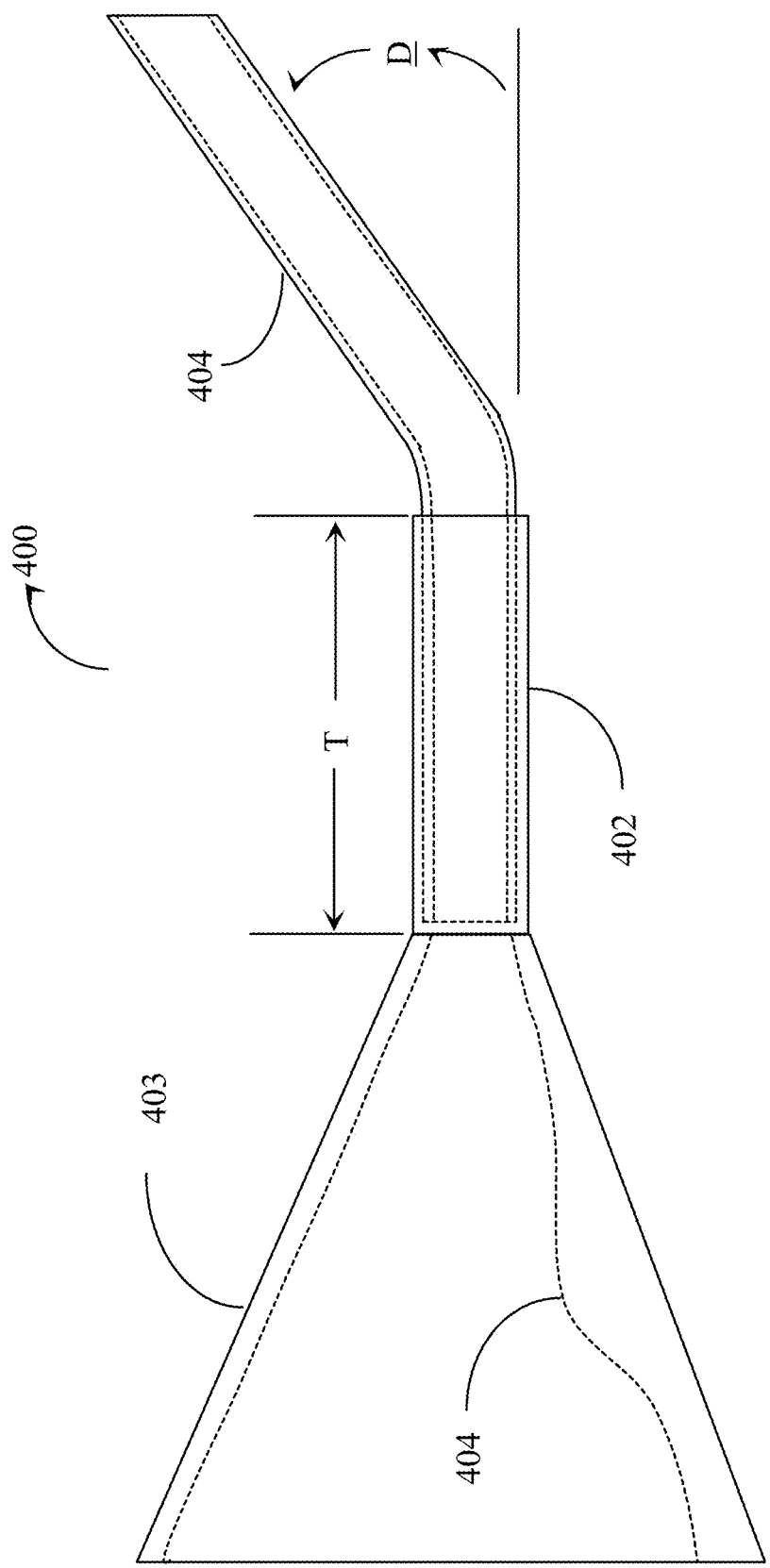
FIG. 4 is an elevation view of a urinary device according to another embodiment of the present invention.

FIG. 4 is an elevation view of a telescopic urinary device 400 with a male attachment. Device 400 comprises a tubing section 404 of a specific diameter and a tubing section 402 having a specific diameter just larger than the diameter of section 404 to provide for telescopic assembly and use. Device 400 may be telescopically collapsed when not in use. A length T illustrates a length defining the added or retracted length of device 400.

In this example, device 400 as a male attachment cup 403 that can be used in place of cup 107 in an embodiment where device 400 can be used by a male or a female. Cup 403 is in the general shape of a cone and may be formed using a molding process. The conical shape of cup 403 should not be construed as a limitation. Cup 403 may also be generally cylindrical in shape. Cup 403 may have a shaped wall 404 provided thereto to conform to a male anatomy, specifically testicular anatomy. A formed portion of cup 403 such as wall 404 may serve to add a level of comfort to the user and to help prevent splash back of urine while in use. Device 400 may also include a gutter as described further above for device 100.

Device 400 may be configured back into a female urination device by removing cup 403 and adding the female cup attachment 107 and the other attachments like the shield and the support rib if provided.

In a further aspect of the invention a trouser garment for use by women, specifically adapted to be used with the device depicted in FIGS. 1-4, and described herein with reference to those figures, is provided, having an especially configured, and especially placed opening to accommodate the urinary device.

Figure 5:
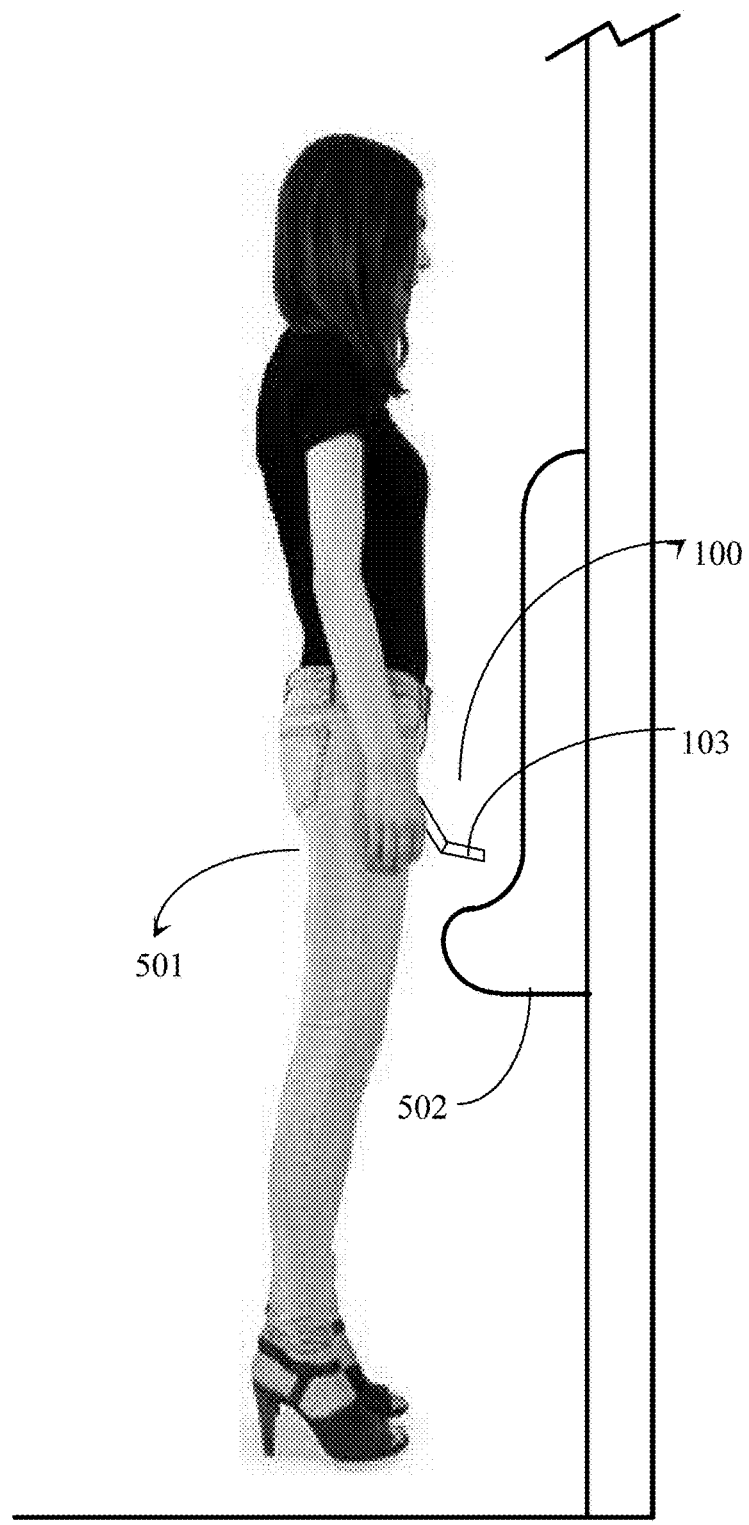
FIG. 5 is a perspective drawing of a trouser garment meant for use by a woman, adapted for use with the device depicted in FIGS. 1-4.

FIG. 5 illustrates a side view elevation of a woman wearing a trouser garment 501 according to an embodiment of the invention, standing in front of a urinal 502, having placed device 100 through an opening (not seen in FIG. 5) in the garment and positioned same against the urethra with the end of tube 103 over the urinal.

Figure 6:
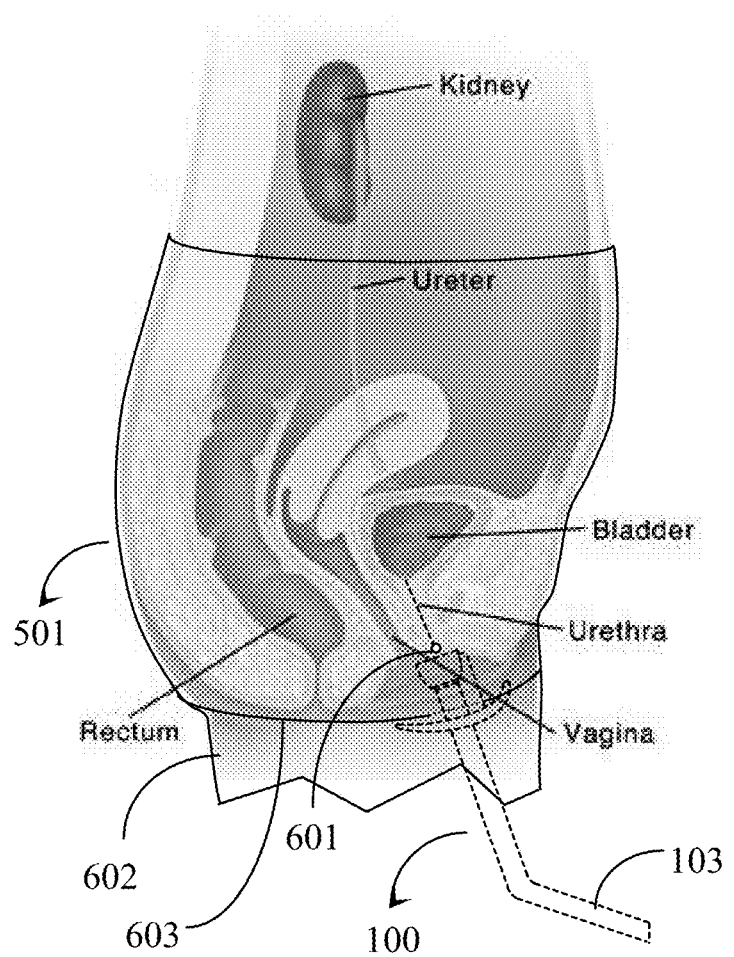
FIG. 6 is a side elevation view of a woman's anatomy relative to the garment of FIG. 5.

FIG. 6 is a side elevation view of a woman's anatomy relative to the garment 501 of FIG. 5. Garment 501 is shown in solid outline in FIG. 6 in order that the spatial relationship between the anatomy and the garment may be better understood. Line 603 represents the crotch area of garment 501 at the point that the legs 602 join to upper portions of the garment. The bladder and the urethra are shown, the urethra ending at a point 601. A urinary device 100 as described above is illustrated as placed in position such that the receiving cup of the device is engaged over the opening from the urethra, and the shield 105 is outside the garment.

An opening in the crotch area of the garment, termed a Wee-Fly by the inventor, is implemented to allow the user to insert the receiving cup 107 of device 100. This opening is shown in FIG. 6 along crotch line 603 as a dotted break in line 603 centered on the center of the tubing that proceeds from cup 107. This opening may be a fly opening with a flap, with a fly length of about 1½ inches, such that the user may use the cup 107 of device 100 to engage the opening and insert the cup to engage over the opening of the urethra, with shield 105 contacting the body outside garment 501. When this is accomplished the user may urinate without any disrobing, and in a standing position. When finished the user may simply remove the urinary device 100, and clean the device.

Figure 7A:
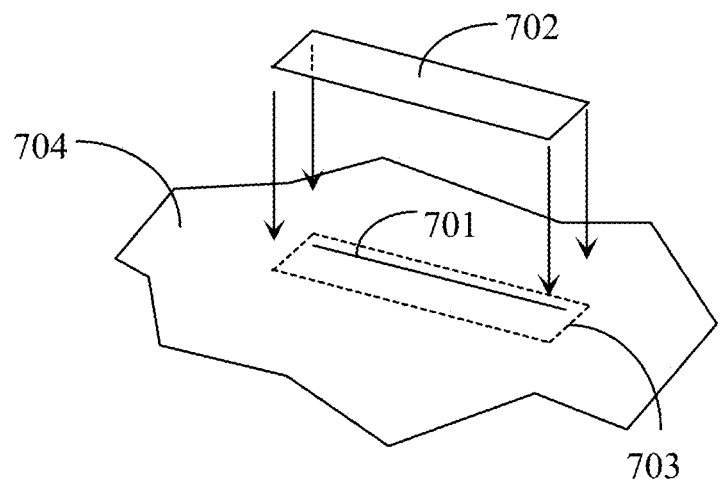
FIG. 7A is one view of a fly arrangement according to an embodiment of the present invention.

The approximate position of the Wee Fly is apparent from FIG. 6. FIG. 7A is a perspective view describing construction of a Wee Fly opening in an embodiment of the present invention. In FIG. 7A a rectangle of fabric 702 (flap) is shown suspended above a crotch region 704 of garment 501. A slit of about 1½ inch length is made in the fabric of the crotch region. Flap 702 is placed over slit 701 at position 703 shown as a dotted rectangle.

Figure 7B:
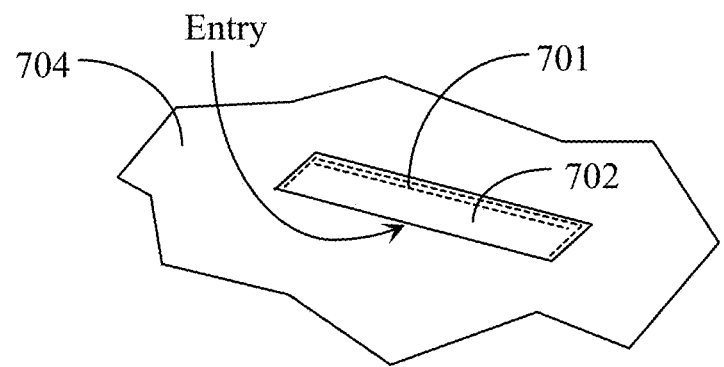
FIG. 7B is another view of a fly arrangement according to an embodiment of the present invention.

FIG. 7B shows flap 702 stitched to fabric of crotch region 704 on three sides. This construction creates an opening through the crotch region that may be accessed along the action line of the arrow labeled "entry". The user may use the receiving cup and of the urinary device to engage the open side of the Wee Fly flap, and move the cup under the flap and through slit 701 to engage the opening from the urethra. After use the urinary device may be removed the same way.

Figure 8:
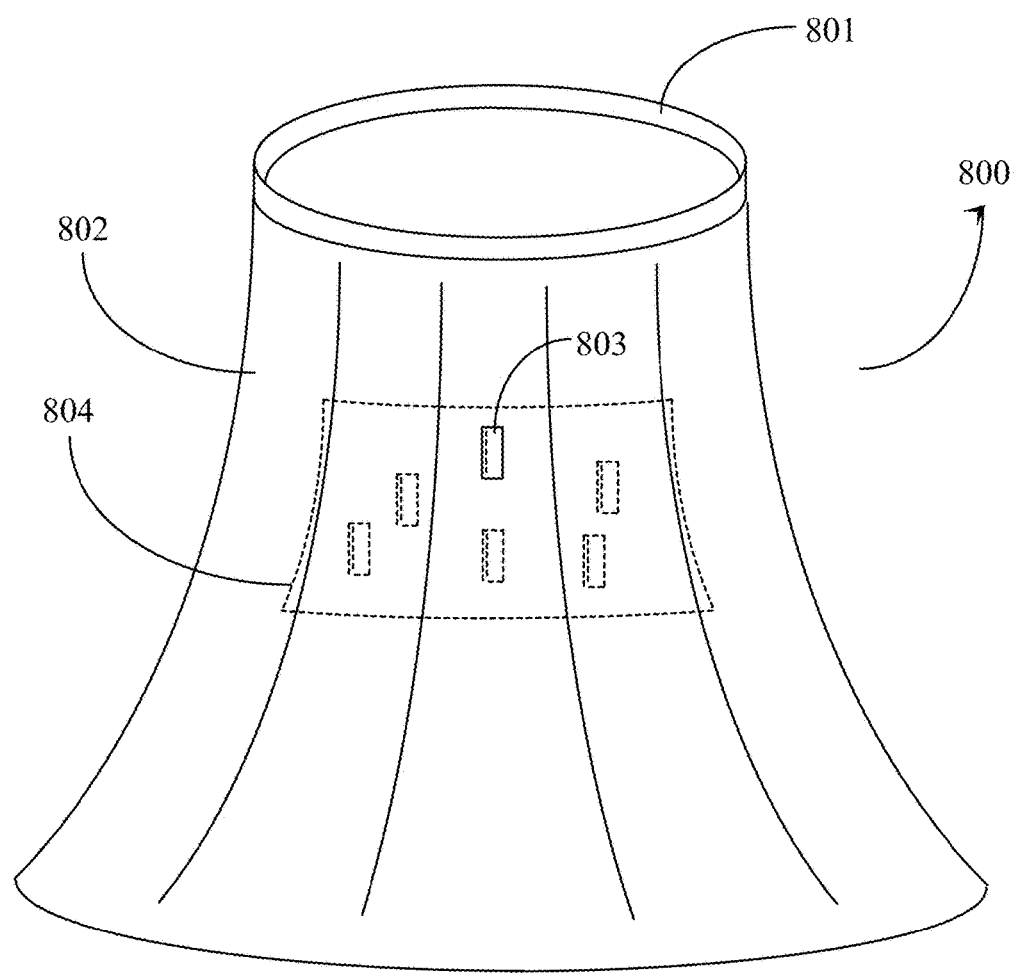
FIG. 8 is an elevation view of a garment showing fly positions according to an embodiment of the present invention.

FIG. 8 is an elevation view of a skirt garment 800 having a waistband 801 and a fabric skirt 802. A fly 803 of the design described with regard to FIGS. 7A and 7B is provided at a position on a front area of the skirt low enough that a device of the sort taught in this specification may be inserted through the fly opening and positioned over the urethra of the person wearing the skirt.

A fly may be provided in the skirt in a variety of places, some as shown within a boundary denoted by dotted area

804, as long as the skirt, being loose, may be pulled one way or another so that the urinary device may be properly placed. In some cases the fly may be in the back of the skirt, and in some cases in both the front and the back. In most cases, by using fabric and stitching thread of a common color with the skirt, the fly me be unobtrusive or nearly invisible.

Skirt 800 is meant to represent skirts of all types, both fitted, tight and loose, and skirt extensions of dresses as well.

In some instances, a person may prefer a lighter solution, or an establishment may provide a urinary device to the person for use. In this case, it may be advisable to have a single-use option that may be manufactured inexpensively, as well as be manufactured from a biodegradable material to reduce waste.

Figure 9:
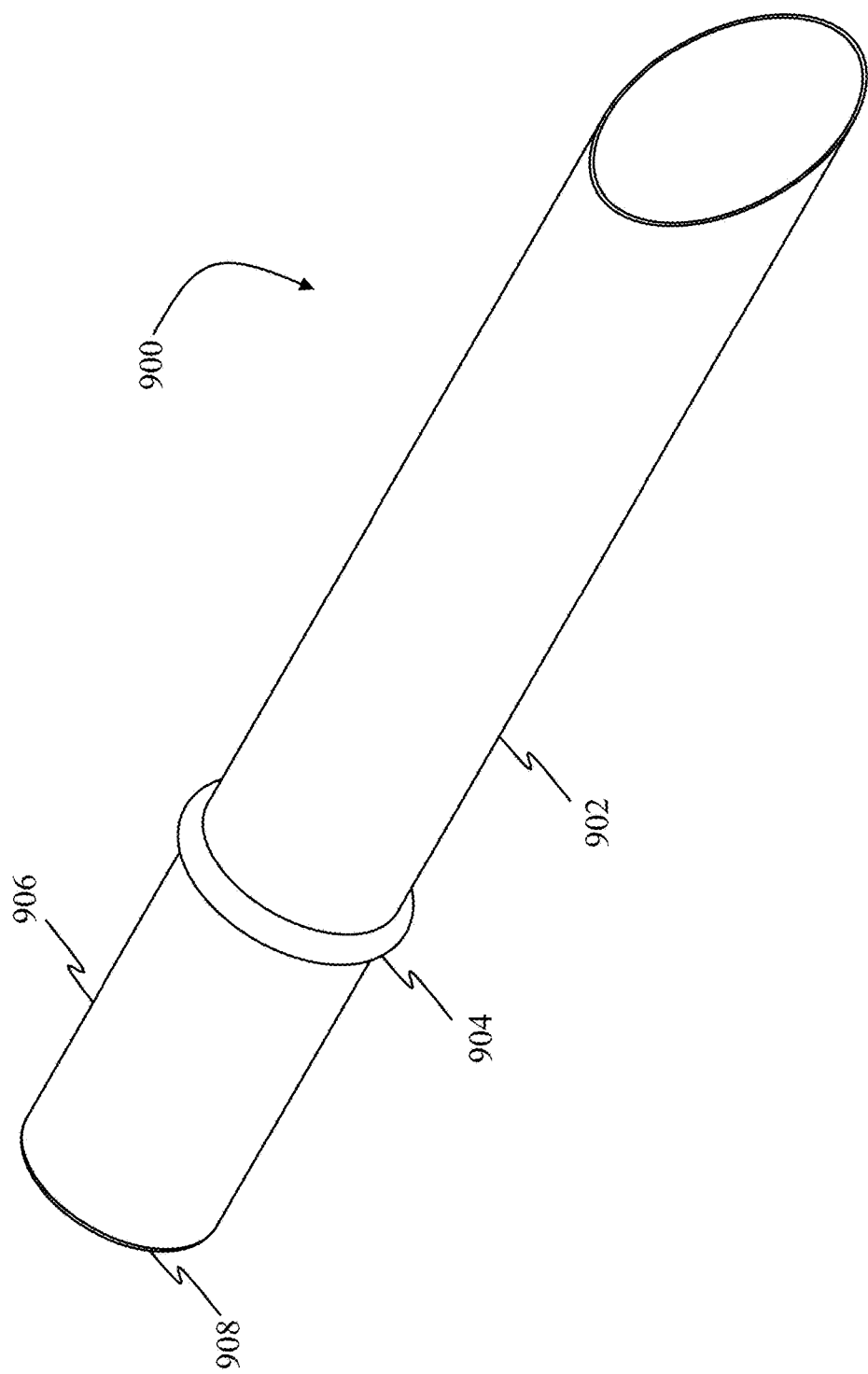
FIG. 9 is a front perspective view of a disposable female urinary device according to one embodiment of the invention.
Figure 11A:
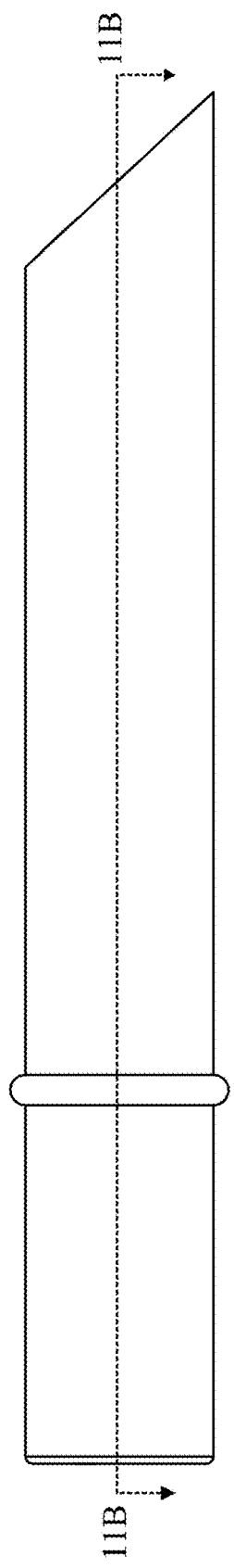
FIG. 11A is an elevation view of the device of FIG. 9.

FIG. 9 is a front isometric view of a female urinary device 900 according to one embodiment of the present invention. FIG. 10 is a rear isometric view of urinary device 900, and FIG. 11A is an elevation view of urinary device 900. Urinary device 900, unlike the urinary device in previously described embodiments in this specification, may be constructed inexpensively from a piece of biodegradable material, and may be disposed of after a single use. Urinary device 900 may, for example, be constructed from smooth cardboard or paperboard, in some embodiments with a liquid-resistant layer, such as the material used to construct paper cups. This material may be rolled and pasted along opposite edges to form a cylindrical shape. The device may also be made of extruded plastic in some embodiments, similar to a drinking straw. Urinary devices according to these disposable embodiments may come individually packaged to ensure sanitary standards are maintained. Urinary device 900 may have an external section 902, a positioning rib 904, an internal section 906, and a rounded end 908.

In embodiments of the invention described with reference to FIGS. 9 through 12, the wall thickness of the tube may be relatively thin, such as 1/32 inch (about 0.8 mm), with a length that may vary from about 6 inches to 12 inches, and a diameter that may be from 3/8 of an inch to about 3/4 of an inch in some embodiments. In paper, paperboard and cardboard implementations the tube may be coated on the inside and/or the outside with a lacquer, or other waterproofing coating.

External section 902 remains outside of the female genitalia during use to lead liquid expelled during urination away from the user's urethra, and to enable the user to more accurately direct the liquid, either into a urine receptacle or a specific spot, such as a bush if the user is camping in the wilderness.

Figure 11B:
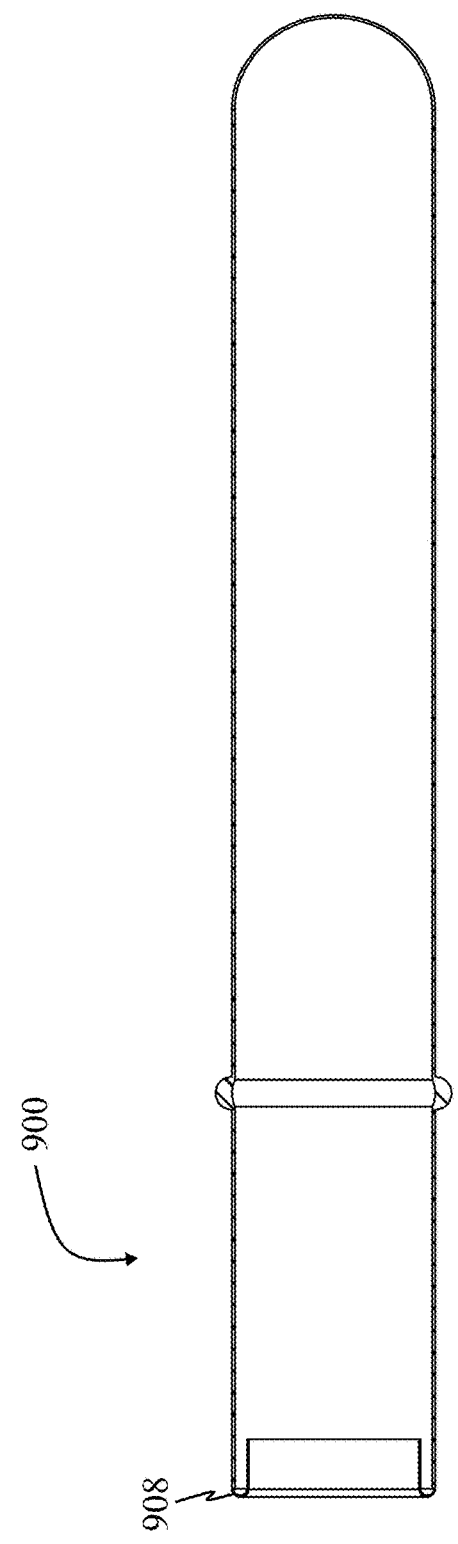
FIG. 11B is a cross-section along the line labeled 11B from FIG. 11A.

Internal section 906 may be inserted into the female genitalia during use, and rounded end 908 may fit snugly and comfortably around the urethra. The rounded nature of rounded end 908 may contribute to the overall comfort during use. Rounded end 908 may be formed during manufacturing by folding or rolling the end of device 900 into the body of tube section 906. This is shown in FIG. 11B, which is a cross-section view of urinary device 900. In other embodiments, the rounded end may be created by a secure placement of a smooth plastic cap, which is detailed below and shown in FIG. 12.

In between external section 902 and internal section 906, there may be a positioning rib 904, as described above. Positioning rib 904 may serve as a holding rib for urinary device 900, and provide a point of reference for finger placement, and insertion depth for the user. In this embodiment, positioning rib 904 may be formed from indentations formed on the construction material, and need not be a separately manufactured article. However, it should be understood that other embodiments may have a separately manufactured positioning rib, to allow a user to slide the rib along the tube to adjust to personal needs.

Figure 12:
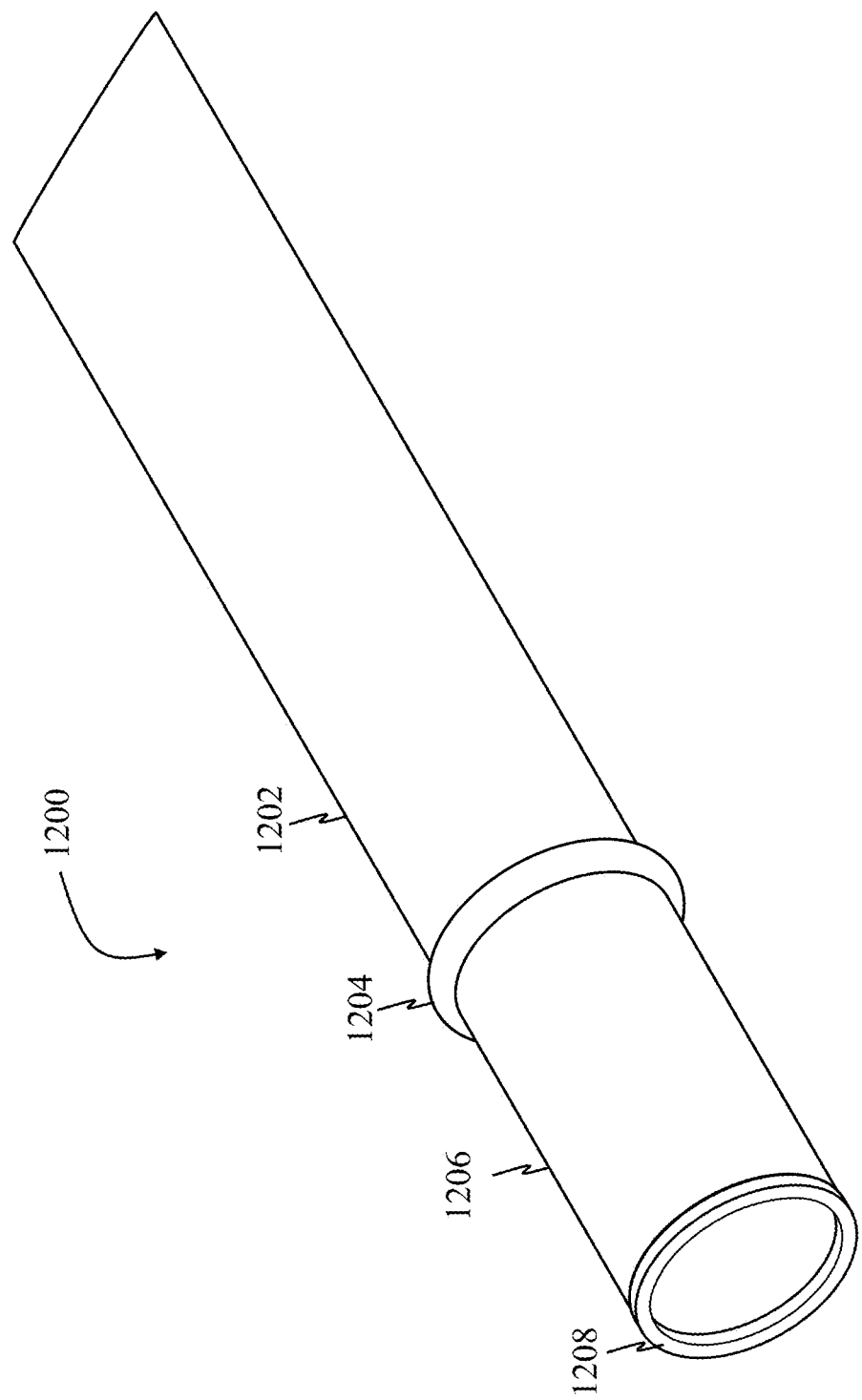
FIG. 12 is perspective view of a disposable female urinary device according to another embodiment of the invention.

FIG. 12 is an isometric view of a female urinary device 1200 according to another embodiment of the present invention. Functionally, urinary device 1200 may be identical to urinary device 900, and may have many of the same parts: an external section 1202 which is similar to external section 902, a positioning rib 1204 which is similar to position rib 904, and an internal section 1206 which is similar to internal section 906. One difference is that device 1200, instead of having a smooth end formed from the folding or rolling of the construction material, has a smooth cap 1208. Smooth cap 1208 may be constructed from any material used to construct urinary device 100 as listed above, such as medical-grade polymer, or some metals and ceramics. Cap 1208 may be constructed through injection molding, or heat-formed onto the end of urinary device 1200, and secured onto the of urinary device 1200 to ensure that cap 1208 does not become dislodged during normal use.

The skilled person will be aware that the drawings and descriptions provided in this application describe embodiments of the present invention, but not all possible embodiments. There may be variations in the various descriptions falling still within the scope of the invention. The scope of the invention is limited only by the claims below.

The invention claimed is:

1. A personal urinary device for a female, comprising:
   a straight, cylindrical tube having a long axis and an outside diameter, the tube made of biodegradable material, the tube having a first end and a second end, the second end forming an angle greater than zero degrees with a plane perpendicular to the long axis of the tube;
   a positioning rib having a diameter larger than the outside diameter of the tube and a length in the direction of the axis of the tube, formed on the outside diameter of the tube, dividing the tube into an internal section having a length from the positioning rib to the first end, and an external section having a length from the rib to the second end, the length of the internal section less than the length of the external section, and the length of the rib being substantially less than the length of either the internal or the external section.

2. The device of claim 1 wherein the tube is formed by rolling a flat sheet of paper or paperboard having a length to be the length of the tube, and a width to provide the circumference of the tube, curved on a first end, into a tube, and securing two long edges after rolling with an adhesive.

3. The device of claim 2 wherein the positioning rib is formed by a length of material secured across the flat sheet by an adhesive, before rolling the flat sheet into the tube.

4. The device of claim 2 wherein the first end is formed with a double thickness by folding the width at the end of the flat sheet to the inside prior to rolling the sheet.

5. The device of claim 1 wherein the tube is coated on the outside by a waterproof material.

6. The device of claim 1 wherein the tube is coated on both inside and outside by a waterproof material.

7. The device of claim 1 wherein the positioning rib is implemented at from about three quarters of one inch to about two inches from the first end.

8. The device of claim 1 wherein a rounded element as a separate piece is assembled to the first end.

9. The device of claim 1 wherein the straight, cylindrical tube is formed by extrusion from plastic.

10. A method for forming a personal urinary device for a female, comprising:

forming a straight, cylindrical tube having a long axis and an outside diameter, the tube made of biodegradable material, the tube having a first end and a second end, the second end forming an angle greater than zero degrees with a plane perpendicular to the long axis of the tube;

implementing a positioning rib having a diameter larger than the outside diameter of the tube and a length in the direction of the axis of the tube, formed on the outside diameter of the tube, dividing the tube into an internal section having a length from the positioning rib to the first end, and an external section having a length from the rib to the second end, the length of the internal section less than the length of the external section, and the length of the rib being substantially less than the length of either the internal or the external section.

11. The method of claim 10 wherein the tube is formed by rolling a flat sheet of paper or paperboard having a length to be the length of the tube, and a width to provide the circumference of the tube, curved at one on a first end into a tube, and joining the long edges after rolling with an adhesive.

12. The method of claim 11 wherein the positioning rib is formed by a length of material secured across the flat sheet by an adhesive, before rolling the flat sheet into the tube.

13. The method of claim 11 wherein the first end is formed with a double thickness by folding the width at the end of the flat sheet to the inside prior to rolling.

14. The method of claim 10 wherein the tube is coated on the outside by a waterproof material.

15. The method of claim 10 wherein the tube is coated on both inside and outside by a waterproof material.

16. The method of claim 10 wherein the positioning rib is implemented at from about three quarters of one inch to about two inches from the first end.

17. The method of claim 10 wherein a rounded element as a separate piece is assembled to the first end.

18. The method of claim 10 wherein the straight, cylindrical tube is formed by extrusion from plastic.

\* \* \* \* \*